(12) United States Patent
Lum et al.

(10) Patent No.: US 7,727,740 B1
(45) Date of Patent: Jun. 1, 2010

(54) METHODS FOR DETERMINING WHETHER A CHEMICAL AGENT MODULATES ENZYMATIC ACTIVITY OF AN L-2-HYDROXY ACID OXIDASE

(75) Inventors: Pek Yee Lum, Seattle, WA (US); Rebecca Kaplan, Parsippany, NJ (US); Tian-Quan Cai, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 11/490,840

(22) Filed: Jul. 21, 2006

Related U.S. Application Data (60) Provisional application No. 60/701,589, filed on Jul. 22, 2005.

(51) Int. Cl.
*C12Q 1/26* (2006.01)
*A61K 49/00* (2006.01)

(52) U.S. Cl. .......................................... 435/25; 424/9.2
(58) Field of Classification Search ........................ None
See application file for complete search history.

(56) References Cited

U.S. PATENT DOCUMENTS

| 6,673,549 B1 | 1/2004 | Furness |
|---|---|---|
| 2003/0055019 A1 | 3/2003 | Shimkets |

OTHER PUBLICATIONS

Ferjancic-Biagini et al. Inhibitory Effects of Anions and Active Site Amino Acid Sequence of Chicken Liver L-2-Hydroxyacid Oxidase A, A Member of the FMN-Dependent Alpha-Hydroxyacid Oxidizing Family; Biochimie, vol. 80 (1998) pp. 1047-1054.*

Robinson et al. L-Alpha-Hydroxy Acid Oxidases of HOG Renal Cortex; The Journal of Biological Chemistry, vol. 237, No. 6 (1962) pp. 2001-2010.*

Schwam et al., Purification and characterization of human liver glycolate oxidase. Molecular weight, subunit, and kinetic properties; Biochemistry, vol. 18, Issue 13, pp. 2828-2833.*

Robinson et al. L-Alpha-Hydroxy Acid Oxidases of HOG Renal Cortex; The journal of Biological Chemistry, vol. 237, No. 6 (1962) pp. 2001-2010.*

Schwam et al. Purification and Characterization of Human Liver Glycolate Oxidase. Molecular Weight, Subunit, and Kinetic Properties; Biochemistry, vol. 18, No. 3 (1979) pp. 2828-2833.*

Jones, J.M., et al., "Identification and Characterization of HAOX1, HAOX2, and HAOX3, Three Human Peroxisomal 2-Hydroxy Acid Oxidases," *J. of Biol. Chem.* 275(17):12590-12597, Apr. 28, 2000.

Schadt, E.E., et al., "Genetics of Gene Expression Surveyed in Maize, Mouse and Man," *Nature* 422:297-302, Mar. 20, 2003.

Belmouden, A., et al., "Molecular Cloning and Nucleotide Sequence of cDNA Encoding Rat Kidney Long-Chain L-2-Hydroxy Acid Oxidase Expression of the Catalytically Active Recombinant Protein as a Chimaera," Eur. J. Biochem. 214(1):17-25, May 1993.

Diêp Lê, K.H., and F. Lederer, "Amino Acid Sequence of Long Chan α-Hydroxy Acid Oxidase From Rat Kidney, a Member of the Family of FMN-Dependent α-Hydroxy Acid-Oxidizing Enzymes," J. Biol. Chem. 266(31):20877-20881, Nov. 1991.

Duley, J.A., and R.S. Holmes, "L-α-Hydroxyacid Oxidase Isozymes: Purification and Molecular Properties," Eur. J. Biochem. 63(1):163-173, Mar. 1976.

Fry, D.W., and K.E. Richardson, "Isolation and Characterization of Glycolic Acid Oxidase From Human Liver," Biochimica et Biophysica Acta 568(1):135-144, May 1979.

Gadegbeku, C.A., "Hemodynamic Effects of Nicotinic Acid Infusion in Normotensive and Hypertensive Subjects," Amer. J. Hypertension 16(1):67-71, Jan. 2003.

Holmes, R.S., "Genetics of Hydroxyacid Oxidase Isozymes in the Mouse: Localisation of Hao-2 on Linkage Group XVI," Heredity 41(3):403-406, Dec. 1978.

Holmes, R.S., "The Genetics of α-Hydroxyacid Oxidase and Alcohol Dehydrogenase in the Mouse: Evidence for Multiple Gene Loci and Linkage Between Hao-2 and Adh-3," Genetics 87(4):709-716, Dec. 1977.

Kohler, S.A., et al., "Molecular Cloning of Mouse Glycolate Oxidase," J. Biol. Chem. 274(4):2401-2407, Jan. 1999.

Korstanje, R., et al., "Quantitative Trait Locus Mapping of Genes That Regulate Phospholipid Transfer Activity in SM/J and NZB/BINJ Inbred Mice," Arterioscler. Thromb. Vasc. Biol. 24(1):155-160, Jan. 2004.

Lee, S.J., et al., "Use of a Panel of Congenic Strains to Evaluate Differentially Expressed Genes as Candidate Genes for Blood Pressure Quantitative Trait Loci," Hypertens. Res. 26(1):75-87, Jan. 2003.

Miles, J.L., and R.S. Holmes, "The Ontogeny of L-α-Hydroxyacid Oxidase Isozymes in the Mouse," Journal of Experimental Zoology 192(1):119-125, Apr. 1975.

Schuman, M., and V. Massey, "Purification and Characterization of Glycolic Acid Oxidase From Pig Liver," Biochimica et Biophysica Acta 227(3):500-520, Mar. 1971.

Schwam, H., et al., "Purification and Characterization of Human Liver Glycolate Oxidase. Molecular Weight, Subunit, and Kinetic Properties," Biochem. 18(13)2828-2833, Jun. 1979.

(Continued)

*Primary Examiner*—Rebecca E. Prouty
*Assistant Examiner*—Paul C. Martin
(74) *Attorney, Agent, or Firm*—Christensen O'Connor Johnson Kindness PLLC (57) ABSTRACT

The present invention provides methods for screening for one or more chemical agents that modulate the enzymatic activity of an L-2-hydroxy acid oxidase. The methods comprise the steps of (a) contacting an L-2-hydroxy acid oxidase, in a solution in vitro, with one or more chemical agents in the presence of a substrate that is capable of being oxidized by the L-2-hydroxy acid oxidase; (b) measuring the enzymatic activity of the L-2-hydroxy acid oxidase in the presence of the chemical agent to identify one or more candidate chemical agents that modulate L-2-hydroxy acid oxidase activity in vitro; and (c) administering the one or more identified candidate chemical agents to a test animal and measuring one or more physiological parameters.

13 Claims, 2 Drawing Sheets

OTHER PUBLICATIONS

Sorrentino, R., and A. Pinto, "Effect of Methylguanidine on Rat Blood Pressure: Role of Endothelial Nitric Oxide Synthase," British J. Pharmacology 115(3):510-514, Jun. 1995.

Sorrentino, R., and A. Pinto, "The Increase in Blood Pressure Induced by Inhibition of Nitric Oxide Synthase in Anesthetized Wistar Rats Is Inversely Related to Basal Blood Pressure Valve," J. Cardiovascular Pharmacology 29 (5):599-604, May 1997.

Takemura, K., et al., "Biosynthesis of Methylguanidine in the Hepatic Peroxisomes and the Effect of the Induction of Peroxisomal Enzymes by Clofibrate," Nephron 78(1):82-87, May 1998.

Van Veldhoven, P.P., et al., "Further Insights Into Peroxisomal Lipid Breakdown via $\alpha$- and $\beta$- Oxidation," Biochemical Society Transactions 29(pt. 2):292-298, May 2001.

* cited by examiner

METHODS FOR DETERMINING WHETHER A CHEMICAL AGENT MODULATES ENZYMATIC ACTIVITY OF AN L-2-HYDROXY ACID OXIDASE

CROSS-REFERENCE(S) TO RELATED APPLICATION(S)

This application claims the benefit of U.S. Provisional Application No. 60/701,589, filed Jul. 22, 2005.

FIELD OF THE INVENTION

The present application relates to methods for screening for a chemical agent that modulates the enzymatic activity of an L-2-hydroxy acid oxidase, and for identifying therapeutic agents useful for treating Metabolic Syndrome.

BACKGROUND

Metabolic Syndrome is an increasingly common disease that is characterized by a group of metabolic risk factors that include: excessive fat tissue in and around the abdomen; blood fat disorders (e.g., high triglycerides and low HDL cholesterol) that foster plaque accumulation in artery walls; raised blood pressure (typically 130/85 mm Hg, or higher); insulin resistance or glucose intolerance; an increased tendency to form blood clots (e.g., due to high fibrinogen or plasminogen activator inhibitor 1 in the blood); and elevated levels of proinflammatory proteins (e.g., elevated level of C-reactive protein in the blood).

The development of this syndrome is promoted by obesity, physical inactivity and genetic factors. People with Metabolic Syndrome are at increased risk of coronary heart disease, other diseases related to plaque accumulation in artery walls (e.g., stroke and peripheral vascular disease) and Type II diabetes.

The genetic factors that contribute to Metabolic Syndrome are not yet understood. Consequently, there is a need to identify genes that contribute to the development of Metabolic Syndrome. There is also a need for methods that permit the identification of chemical agents that modulate the activity of these genes, or the products encoded by these genes. Such chemical agents may be useful, for example, as drugs to prevent Metabolic Syndrome, or to ameliorate one or more symptoms of Metabolic Syndrome.

SUMMARY

As described more fully herein, L-2-hydroxy acid oxidases are involved in lipid biochemistry. The present inventors have observed a correlation between the expression of an L-2-hydroxy acid oxidase gene (called Hao 3) and certain metabolic and physical traits that are associated with Metabolic Syndrome. These traits include body weight, the amount of retroperitoneal fat in the abdomen, and the level of leptin (a hormone that contributes to the control of appetite in mammals) in the blood. Modulation of the activity of L-2-hydroxy acid oxidases in mammals may, therefore, delay or prevent the onset of Metabolic Syndrome, or ameliorate one or more symptoms of Metabolic Syndrome.

Thus, in one aspect, the present invention provides methods for screening for one or more chemical agents that modulate the enzymatic activity of an L-2-hydroxy acid oxidase, the method comprising the steps of: (a) contacting an L-2-hydroxy acid oxidase, in a solution in vitro, with one or more chemical agents in the presence of a substrate that is capable of being oxidized by the L-2-hydroxy acid oxidase; (b) measuring the enzymatic activity of the L-2 hydroxy acid oxidase in the presence of the chemical agent to identify one or more candidate chemical agents that modulate L-2 hydroxy acid oxidase activity in vitro; and (c) administering the one or more identified candidate chemical agents to a test animal and measuring one or more physiological parameters selected from the group consisting of body weight, body fat, retroperitoneal fat accumulation, serum level of LDL-cholesterol, serum level of HDL-cholesterol, leptin expression, and blood pressure, wherein a change in one or more physiological parameters relative to an animal not administered the candidate chemical agent is indicative of the identified candidate chemical agent possessing the ability to modulate enzymatic activity of an L-2-hydroxy acid oxidase in vivo.

In another aspect, the present invention provides methods for screening for one or more chemical agents useful for ameliorating at least one symptom of Metabolic Syndrome, the method comprising: (a) screening for one or more candidate chemical agents that inhibit the enzymatic activity of an L-2-hydroxy acid oxidase in a solution in vitro; and (b) administering the inhibitory candidate chemical agents to a test animal and measuring one or more physiological parameters associated with Metabolic Syndrome, wherein a change in one or more physiological parameters relative to an animal not administered the inhibitory candidate chemical agent is indicative of utility in ameliorating at least one symptom of Metabolic Syndrome.

The methods of the present invention are useful, for example, for identifying candidate, therapeutic, chemical agents that delay or prevent the onset of Metabolic Syndrome, or ameliorate one or more symptoms of Metabolic Syndrome. The methods of the invention are also useful for identifying chemical agents that modulate (e.g., stimulate or inhibit) the activity of L-2-hydroxy acid oxidases, and that can be used to further elucidate the biological role of L-2-hydroxy acid oxidases in lipid biochemistry in mammals.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The present invention provides methods for screening for one or more chemical agents that modulate the enzymatic activity of an L-2-hydroxy acid oxidase, the method comprising the steps of: (a) contacting an L-2-hydroxy acid oxidase, in a solution in vitro, with one or more chemical agents in the presence of a substrate that is capable of being oxidized by the L-2-hydroxy acid oxidase; (b) measuring the enzymatic activity of the L-2 hydroxy acid oxidase in the presence of the chemical agent to identify one or more candidate chemical agents that modulate L-2 hydroxy acid oxidase activity in vitro; and (c) administering the one or more identified candidate chemical agents to a test animal and measuring one or more physiological parameters selected from the group consisting of body weight, body fat, retroperitoneal fat accumulation, serum level of LDL-cholesterol, serum level of HDL-cholesterol, leptin expression, and blood pressure, wherein a change in one or more physiological parameters relative to an animal not administered the candidate chemical agent is indicative of the identified candidate chemical agent possessing the ability to modulate enzymatic activity of an L-2-hydroxy acid oxidase in vivo.

As used herein, the term "chemical agent" encompasses any chemical molecule or chemical element, or combination of chemical molecules and/or chemical elements. For example, the term "chemical agent" encompasses proteins (comprising at least 100 covalently linked amino acid units) and peptides (comprising from two to 99 covalently linked amino acid units).

As used herein, the term "L-2-hydroxy acid oxidase" refers to an enzyme that oxidizes a 2-hydroxy acid to form a 2-keto acid with the concomitant reduction of molecular oxygen to hydrogen peroxide. Examples of 2-hydroxy acids that can be oxidized by an L-2-hydroxy acid oxidase include glycolate, L-2 hydroxy-octanoate, mandelate, and long chain 2-hydroxy fatty acids, such as 2-hydroxypalmitate. L-2-hydroxy acid oxidases use a flavin cofactor. By way of example, SEQ ID NO:1 sets forth the sequence of an mRNA molecule (isolated from *Mus musculus*, and publicly available in the GENBANK® database under accession number NM 019545.2, also listed in GENBANK® as AK018684) that encodes the L-2-hydroxy acid oxidase (referred to as Hao3) having the amino acid sequence set forth in SEQ ID NO:2. Again by way of example, SEQ ID NO:3 sets forth the sequence of an mRNA molecule (isolated from *Rattus norvegicus*, and publicly available in the GENBANK® database under accession number NM 032082.1) that encodes the L-2-hydroxy acid oxidase (referred to as Hao2) having the amino acid sequence set forth in SEQ ID NO:4. By way of further example, SEQ ID NO:5 sets forth the sequence of an mRNA molecule (isolated from *Homo sapiens*, and publicly available in the GENBANK® database under accession number NM 016527.2) that encodes the L-2-hydroxy acid oxidase (referred to as Hao2) having the amino acid sequence set forth in SEQ ID NO:6.

In one embodiment, L-2-hydroxy acid oxidases useful in the practice of the present invention are at least 70% identical (e.g., at least 80% identical, or at least 90% identical, at least 95% identical, at least 99% identical) to the L-2-hydroxy acid oxidase having the amino acid sequence set forth in SEQ ID NO:2, while retaining enzymatic activity.

In another embodiment, L-2-hydroxy acid oxidases useful in the practice of the present invention are at least 70% identical (e.g., at least 80% identical, or at least 90% identical, at least 95% identical, at least 99% identical) to the L-2-hydroxy acid oxidase having the amino acid sequence set forth in SEQ ID NO:6, while retaining enzymatic activity.

The term "percent identity" or "percent identical" when used in connection with the L-2-hydroxy acid oxidases used in the present invention, is defined as the percentage of amino acid residues in a candidate protein sequence, that are identical with a subject protein sequence (such as the amino acid sequence of SEQ ID NO:2 or SEQ ID NO:6), after aligning the candidate and subject sequences to achieve the maximum percent identity. For example, percentage identity between two protein sequences can be determined by pairwise comparison of the two sequences using the bl2seq interface at the website of the National Center for Biotechnology Information (NCBI), U.S. National Library of Medicine, 8600 Rockville Pike, Bethesda, Md. 20894, U.S.A. The bl2seq interface permits sequence alignment using the BLAST tool described by Tatiana A., et al., "Blast 2 Sequences—A New Tool for Comparing Protein and Nucleotide Sequences," *FEMS Microbiol. Lett.* 174:247-250, 1999. The following alignment parameters are used: Matrix=BLOSUM62; Gap open penalty=11; Gap extension penalty=1; Gap×dropff=50; Expect=10.0; Word size=3; and Filter=off.

As used herein, the term "enzymatic activity of an L-2-hydroxy acid oxidase" refers to the ability of an L-2-hydroxy acid oxidase to oxidize a 2-hydroxy acid and thereby form a 2-keto acid.

Modulation of the enzymatic activity of an L-2-hydroxy acid oxidase encompasses any change in the enzymatic activity of the L-2-hydroxy acid oxidase. For example, the change can be a decrease in the enzymatic activity of L-2-hydroxy acid oxidase (e.g., complete, or substantially complete, inhibition of the enzymatic activity of L-2-hydroxy acid oxidase). Again by way of example, the change can be a reduction in the rate of enzymatic activity of L-2-hydroxy acid oxidase. Again by way of example, the change can be an increase in the activity of L-2-hydroxy acid oxidase.

In the practice of the invention, an L-2-hydroxy acid oxidase is contacted, in a solution in vitro, with a chemical agent in the presence of a substrate that is capable of being oxidized by the L-2-hydroxy acid oxidase (such as a 2-hydroxy acid). For example, an L-2-hydroxy acid oxidase can be dissolved in an aqueous solution and a chemical agent can be added to the solution; or an L-2-hydroxy acid oxidase can be added to a solution containing a chemical agent to be tested. The L-2-hydroxy acid oxidase can be completely purified from other components, or partially purified from other components, or can, for example, be present in a crude lysate obtained from cells that express L-2-hydroxy acid oxidase.

L-2-hydroxy acid oxidases useful in the practice of the present invention can be isolated, for example, by expressing nucleic acid molecules encoding an L-2-hydroxy acid oxidase in a suitable host cell, such as *E. coli*. By way of representative example, a nucleic acid molecule (such as a cDNA molecule) encoding an L-2-hydroxy acid oxidase is cloned into a plasmid vector, such as a Bluescript plasmid (available from Stratagene, Inc., La Jolla, Calif.). The recombinant vector is then introduced into an *E. coli* strain (such as *E. coli* XL1-Blue, also available from Stratagene, Inc.) and the protein encoded by the nucleic acid molecule is expressed in *E. coli* and then purified. For example, *E. coli* XL1-Blue harboring a Bluescript vector including a cDNA molecule of interest is grown overnight at 37° C. in LB medium containing 100 µg ampicillin/ml. A 50 µl aliquot of the overnight culture is used to inoculate 5 ml of fresh LB medium containing ampicillin, and the culture grown at 37° C. with vigorous agitation to $A_{600}$=0.5 before induction with 1 mM IPTG. After an additional two hours of growth, the suspension is centrifuged (1000×g, 15 min, 4° C.), the media removed, and the pelleted cells resuspended in 1 ml of cold buffer that preferably contains 1 mM EDTA and one or more proteinase inhibitors. The cells can be disrupted by sonication with a microprobe. The chilled sonicate is cleared by centrifugation and the expressed L-2-hydroxy acid oxidase purified from the supernatant by art-recognized protein purification techniques.

Representative examples of art-recognized techniques for purifying, or partially purifying, proteins from biological material, such as from prokaryotic cells that express the desired protein(s), are: exclusion chromatography, ion-exchange chromatography, hydrophobic interaction chromatography, reversed-phase chromatography and immobilized metal affinity chromatography.

Example 2 herein describes an exemplary method for the expression and purification of exemplary L-2-hydroxy acid oxidase enzymes useful in the practice of the present invention.

Typically, the effect of a chemical agent on the enzymatic activity of the L-2-hydroxy acid oxidase is determined by monitoring the oxidation of a substrate and/or product of a reaction catalyzed by the oxidized substrate (e.g. the coupled reduction of 2,6-dichloroindophenol). For example, if a product of a reaction catalyzed by the oxidized substrate absorbs light at one or more wavelengths is used, then the decrease in the amount of light absorption by the product, as the product is converted, can be measured. Conversely, if the product absorbs light at one or more wavelengths, then the increase in the amount of light absorption by the product, as oxidized substrate converts the product, can be measured.

An assay for assessing the effect of a chemical agent on L-2-hydroxy acid oxidase activity typically includes at least one experimental treatment wherein an L-2-hydroxy acid oxidase is contacted with a chemical agent, and a control treatment wherein an aliquot of the same preparation of L-2-hydroxy acid oxidase used in the experimental treatment is treated identically to the L-2-hydroxy acid oxidase used in the experimental treatment, except that the L-2-hydroxy acid oxidase used in the control treatment is not contacted with the chemical agent. Comparison of the L-2-hydroxy acid oxidase activity in the experimental treatment(s) with the L-2-hydroxy acid oxidase activity in the control treatment(s) permits determination of whether the chemical agent modulates L-2-hydroxy acid oxidase activity. For example, a level of L-2-hydroxy acid oxidase activity that is significantly lower in the experimental treatment(s) compared to the control treatment(s) indicates that the chemical agent inhibits L-2-hydroxy acid oxidase activity. Again by way of example, a level of L-2-hydroxy acid oxidase activity that is significantly higher in the experimental treatment(s) compared to the control treatment(s) indicates that the chemical agent stimulates L-2-hydroxy acid oxidase activity.

Numerous assays (e.g., hundreds or thousands) for assessing the effect of a chemical agent on L-2-hydroxy acid oxidase activity can be automated and conducted simultaneously.

In the practice of the claimed methods, the modulating effect of a chemical agent on L-2-hydroxy acid oxidase is validated in vivo. The in vivo validation comprises administering the one or more candidate chemical agents identified in an in vitro assay to a test animal and measuring one or more physiological parameters associated with Metabolic Syndrome wherein a change in one or more physiological parameters relative to an animal not administered the candidate chemical agent is indicative of the identified candidate chemical agent possessing the ability to modulate enzymatic activity of an L-2-hydroxy acid oxidase in vivo.

The validation step shows that a chemical agent that modulates the activity of L-2-hydroxy acid oxidase in vitro, also causes a significant improvement in a phenotype, in vivo, associated with Metabolic Syndrome (e.g., the chemical agent causes one or more of the following changes: lowers LDL cholesterol, raises HDL cholesterol, lowers body weight, decreases the rate of body weight gain in response to a diet high in fat, decreases insulin resistance, decreases the tendency to form blood clots, and/or decreases the amount of proinflammatory proteins in blood).

Animal models can be used to validate the efficacy of a chemical agent that modulates the activity of L-2-hydroxy acid oxidase in vitro. The chemical agent may be administered to the animal via any suitable route of administration using techniques known to those of skill in the art. For example, the chemical agent may be administered in a pharmaceutical composition. Conventional methods, known to those of ordinary skill in the art of medicine, can be used to administer the pharmaceutical composition to the mammalian subject via conventional routes (e.g., oral, subcutaneous, intrapulmonary, transmucosal, intraperitoneal, intrauterine, sublingual, intrathecal or intramuscular routes) by standard methods. For example, a chemical agent may be combined or admixed with a pharmaceutically acceptable carrier, vehicle or diluent, which may take a wide variety of forms depending on the form of preparation desired for administration. For example, in preparing the compositions in oral dosage form, any of the usual pharmaceutical media may be employed, such as, for example, water, glycols, oils, alcohols, and the like. An exemplary dose of chemical agent is in the range of from about 0.001 to about 200 mg per kg of subject's body weight per day, preferably about 0.05 to 100 mg/kg/day, or about 1 to 35 mg/kg/day. Alternatively, dosages may be administered on a periodic basis, such as once every other day (e.g., from 0.05 to 100 mg/kg every other day).

For example, the effect of a chemical agent on blood pressure can be directly determined using, for example, a radiotelemetry technique (see, e.g., Mills, P. A., et al., "A New Method for Measurement of Blood Pressure, Heart Rate, and Activity in the Mouse by Radiotelemetry," *J. Appl. Physiol.* 88(5):1537-1544, 2000). Again by way of example, the effect of a chemical agent on blood pressure can be indirectly determined using, for example, a tail-cuff technique (see, e.g., Van Vliet, B. N., et al., "Direct and Indirect Methods Used to Study Arterial Blood Pressure," *J. Pharmacol. Toxicol. Methods* 44(2):361-373, 2000).

Again by way of example, the effect of a chemical agent on body weight can be determined using an obesity model wherein obesity is induced by a high fat diet, or by using a obese mutant mouse model (e.g., ob/ob mice) (see, e.g., Tschop, M., and M. L. Heiman, "Rodent Obesity Models: an Overview," *Exp. Clin. Endocrinol. Diabetes,* 109(6):307-319, 2001).

By way of further example, the effect of a chemical agent on a component of Type II diabetes can be measured using a streptozotocin-induced diabetic model, or, for example, by using a spontaneous mutant model such as the obese Zucker rats (fa/fa rats) or the db/db mice (see, e.g., Methe, D., "Dyslipidemia and Diabetes: Animal Models," *Diabetes Metab.* 21(2):106-111, 1995).

In another aspect, the invention provides a method for screening for one or more chemical agent useful for ameliorating at least one symptom of Metabolic Syndrome, the method comprising: (a) screening for one or more candidate chemical agents that inhibit the enzymatic activity of an L-2-hydroxy acid oxidase in a solution in vitro; and (b) administering the inhibitory candidate chemical agents to a test animal and measuring one or more physiological parameters associated with Metabolic Syndrome, wherein a change in one or more physiological parameters relative to an animal not administered the inhibitory candidate chemical agent is indicative of utility in ameliorating at least one symptom of Metabolic Syndrome.

The following examples merely illustrate the best mode now contemplated for practicing the invention, but should not be construed to limit the invention.

Example 1

This example describes the results of the genetic analysis of mice, having altered fat and metabolic characteristics, that shows a positive correlation between Hao 3 gene expression and various traits related to Metabolic Syndrome.

Analysis of data pools from a genetic molecular profiling study of a C57BL/6J×DBA/2J cross indicated that expression of Hao3 may be linked to fat traits and body weight. In this cross study, female C57B1/6J mice were mated to male DBA/2J mice, and the F1s were intercrossed to produce F2 animals. Only female mice from the F2 cross were used for subsequent study. Strain C57BL/6J has an elevated susceptibility to atherosclerosis, while strain DBA/2J has a reduced susceptibility to atherosclerosis. Thus, the progeny of a cross of these two strains include a broad range of susceptibility to atherosclerosis. The F2 mice were fed an atherogenic diet that promotes atherosclerosis. The C57BL/6J and DBA/2J strains, and the atherogenic diet, are described in Schadt, et al., *Nature* 422 (6929):297-302, Mar. 20, 2003, which publication is incorporated herein by reference.

A gene for which there are overlapping expression Quantitative Trait Loci (QTLs) and clinical QTLs with respect to a particular phenotypic trait may be causally related to the trait. Table 1 shows the correlation between expression of the Hao3 gene in the liver and different traits that are relevant to Metabolic Syndrome.

TABLE 1

| gene | trait | corr | pvalues | values used for corr calc |
|---|---|---|---|---|
| AK018684 (Hao3) | livebwt | 0.579935 | 2.46E-11 | 111 |
| AK018684 (Hao3) | retrog | 0.532694 | 2.46E-11 | 69 |
| AK018684 (Hao3) | sqrtretrog | 0.58746 | 1.0736E-07 | 69 |
| AK018684 (Hao3) | sqrtlep | 0.676556 | 8.88E-16 | 108 |
| AK018684 (Hao3) | lep | 0.580113 | 4.54E-11 | 108 |

The following abbreviations are used in Table 1: Livebwt, live body weight; retrog, retroperitoneal fat; sqrtretrog, square root of retroperitoneal fat; lep, leptin; sqrtlep, square root of leptin; con, correlation of gene expression levels to trait; pvalues, significance of correlation; values used for con calc, number of animals used in calculations.

Analysis of the data shown in Table 1 showed that Hao3 gene expression in mouse liver is positively correlated with the traits, related to Metabolic Syndrome, that are listed in Table 1, and may be causal for retroperitoneal fat accumulation and body weight increase in the mice fed anatherogenic diet.

A potential link between expression of Hao3 and certain body fat traits, and body weight, was also discovered by molecular genetic profiling analysis of the data pools from a cross between C57BL/6J apoE−/− mice and C3H apoE−/− mice. Both of these mouse strains have deletions in the ApoE gene, and have an increased tendency to develop atherosclerosis. C57BL/6J apoE−/− mice were purchased from the Jackson Laboratory. C3H apoE−/− mice were generated by backcrossing C57BL/6J apoE−/− mice for 10 generations. F1 mice were generated from reciprocal intercrossing between C57BL/6J apoE−/− mice and C3H apoE−/− mice, and F2 mice were subsequently bred by intercrossing F1 mice.

A total of 334 F2 mice (165 male and 169 female) from this cross were placed on a medium high fat diet for 4 months. The mice were genotyped with respect to about 1500 markers, and liver, adipose tissue and brain were profiled for mRNA expression levels. In addition to fat traits and body weight, a number of other clinical traits, including total cholesterol, triglycerides, and HDL-cholesterol were also scored. These data were used to generate quantitative trait loci (QTLs) for both the traditional clinical values (cQTL) as well as QTLs for gene expression (eQTL). Correlation of expression of a gene to individual traits was also calculated ("trait-gene correlation").

A causal correlation was observed between expression of Hao3 in the liver and various traits associated with Metabolic Syndrome, including the level of leptin expression, the amount of body fat, the amount of retroperitoneal fat, and body weight.

Furthermore, results from this cross study also revealed an inverse correlation between expression levels of Hao3 in the liver and serum levels of HDL-cholesterol and the ratio of HDL/LDL-cholesterol.

A strong gender bias was observed in the genetics of Hao3 in the F2 progeny of the C57BL/6J×DBA/2J cross. Hao3 had many ecQTL overlaps with multiple metabolic traits, but the only overlap that was causal in the C57BL/6J×DBAI2J cross was with total fat in female liver.

Example 2

This example describes the expression and purification of a mouse and human L-2-hydroxy acid oxidase useful in the practice of the present invention.

Preparation of Human Hao2 and Mouse Hao3 Enzymes:

The cDNAs encoding human Hao2 (SEQ ID NO:5) and mouse Hao3 (SEQ ID NO:1) can be purchased from Invitrogen Corporation (Carlsbad, Calif.) These cDNAs encode the full amino acid sequences of a human Hao2 protein (SEQ ID NO:6) and mouse Hao3 protein (SEQ ID NO:2), respectively, and also include a TAG stop codon. The clones are supplied in the Gateway® entry vector, pENTR221, which facilitates the transfer into any of the Gateway® destination vectors. The Gateway® Technology allows for genetic analysis and expression in a multitude of systems (bacterial, mammalian, yeast, or insect).

Site specific recombination occurs between the entry clone and the Gateway® destination vector, pcDNA™ 6.2/GFP-DEST (Invitrogen). This destination vector utilizes the Tag-On-Demand™ system which allows expression of both native and C-terminally-tagged recombinant protein from the same expression construct. Thus, the Hao2 cDNA (SEQ ID NO:5) or Hao3 cDNA (SEQ ID NO:1) entry clones undergo site-specific recombination with the destination vector, pcDNA™ 6.2/GFP-DEST, and the subsequent expression clones are transfected into CHO-K1 cells (ATCC, Manassas, Va.) using the Amaxa nucleofector technology (Amaxa Biosystems, Gaithersburg, Md.) When stable cell lines are created, the protein is constitutively expressed and may be examined by enabling the Tag-On-Demand™ System Suppressor Supernatant (Invitrogen). The Tag-On-Demand™ System allows translation of the TAG stop codon to a serine, thus enabling translation to continue through the GFP coding region of the expression construct. Confocal microscopy may be used to determine recombinant protein localization within the cells.

Similarly, the Hao2 or Hao3 entry clones are recombined with the Gateway®-adapted destination vector pDEST™ 26, fusing a 6x-HIS tag to the N-terminus of the protein. The subsequent pDEST™ 26 expression clone is transfected into CHO-K1 cells and a stable cell line is selected. The 6x-HIS tagged protein is overexpressed and purified using the Pro-Bond™ nickel chelating resin (Invitrogen). The recombinant proteins bound to the resin may be eluted under either native or denaturing conditions for subsequent enzyme characterization.

Cloning of cDNAs Encoding Human Hao2 and Mouse Hao3 Enzymes:

The full length cDNAs encoding human Hao2 (SEQ ID NO:5) and mouse Hao3 (SEQ ID NO:1) were cloned from human or mouse kidney marathon-ready cDNA provided by Clontech (Mountain View, Calif.). These cloned cDNAs encoded the full length amino acid sequences of human Hao2 protein (SEQ ID NO:6) and mouse Hao3 protein (SEQ ID NO:2).

Methods:

The PCR reactions were carried out using the following parameters in a final concentration in a 50111 volume:

1×PCR supermix high fidelity (Invitrogen, Carlsbad, Calif.)

4 µl of species pertinent marathon-ready cDNA 400 nM Forward Primer 400 nM Reverse Primer Mouse Hao2 Primers:

```
                                            (SEQ ID NO: 7)
Forward: 5'-GCGGGATCCATGTCTTTGCTGTGTTTGGCAGACT-3'

(SEQ ID NO: 8)
Reverse: 5'-ATAAGAATGCGGCCGCTTATAATCTGGAGAACTGAAT
CAGGT-3'
```

Human Hao2 Primers:

```
                                            (SEQ ID NO: 9)
Forward: 5'-GCGGGATCCATGTCCTTGGTGTGTCTGACAGAC-3'

(SEQ ID NO: 10)
Reverse: 5'-ATAAGAATGCGGCCGCTTATAATCTGGAGAACTGAAT
CAGGT-3'
```

PCR amplification was carried out as follows: 94° C. for 1 minute followed by: 5 cycles of 94° C. for 30 seconds, 58° C. for 30 seconds, and 72° C. for 2 minutes and 30 seconds, 25 cycles of 94° C. for 30 seconds, 68° C. for 30 seconds, and 72° C. for 2 minutes and 30 seconds and a final extension at 72° C. for 7 minutes.

The human Hao2 and mouse Hao3 cDNA PCR fragments were subsequently purified by the QIAQUICK® PCR purification kit (Qiagen, Valencia, Calif.) to prepare for cloning into a vector. The human Hao2 cDNA was cloned into pMAL-c2E (New England Biolabs, Ipswich, Mass.), and the mouse Hao3 cDNA was cloned into pET28a (Novagen, Madison, Wis.), as described below.

Human Hao2:

Purified, full length cDNA encoding human Hao2 and the vector pMAL-c2E were digested with the restriction enzymes BamHI and Sal I (Invitrogen) overnight at 37° C. The digested human Hao2 and pMAL-c2E vectors were purified after running the fragments on a 1% agarose gel using the DNA gel extraction kit (Millipore, Billerica, Mass.). Human Hao2 was next ligated into pMAL-c2E by T4 DNA ligase (Invitrogen) and transformed into TOP-10 *E. coli* competent cells (Invitrogen) and grown overnight on plates containing LB agar under the selection of 100 µg/ml ampicillin (K-D Medical, Inc. Columbia, Md.) at 37° C. Positive colonies were picked and grown in LB broth containing 100 µg/ml ampicillin to prepare for plasmid purification using QIAPREP® spin miniprep kit (Qiagen). Aliquots of purified plasmids were digested by BamHI and SalI and run on a 1% agarose gel to identify the clones containing the human Hao2 gene. Bacterial clones containing the proper plasmid and human Hao2 insert were grown in 100 ml of LB broth under the selection of 100 µg/ml ampicillin and plasmid DNA was purified using the Qiagen plasmid midi kit and double strand sequenced (Genewiz, Inc., North Brunswick, N.J.) to confirm accuracy. The plasmid containing the full length human Hao2 sequence was called MBP-huHAO2 and contained a maltose binding protein-Hao2 fusion protein.

Purified MBP-huHAO2 expression vector was next transformed into BL21-codonplus-RIPL competent cells (Stratagene, La Jolla, Calif.) and grown overnight in 10 ml LB broth containing 100.1 g/ml ampicillin at 37° C. with constant shaking. 5 ml of the overnight culture was transferred to 500 ml of the same selection medium pre-warmed to 37° C. and incubation continued at 37° C. with shaking until the OD600 reached 0.5-1.0. IPTG was added into the culture at a final concentration of 0.5 mM to induce MBP-huHAO2 expression and the incubation continued at 37° C. for an additional 3 hours with constant shaking. Cells were harvested by centrifugation at 3,000×g for 25 minutes at 4° C. and the pellet was stored at −80° C.

The BL21 cell pellet containing MBP-huHAO2 (net weight 6-8 g) was resuspended in 35 ml of ice cold column buffer (20 mM Tris-HCl pH 7.5, 200 mM NaCl, 1 mM EDTA, provided by Sigma-Aldrich, St. Louis, Mo.) supplemented with 0.4 ml protease inhibitor cocktail set II (Calbiochem, San Diego, Calif.) and lysed by French Press at 4° C. The cell lysate was then centrifuged at 12,000×g for 30 minutes at 4° C. and the supernatant was transferred to a fresh 50 ml Falcon tube (BD Biosciences, Bedford, Mass.) and stored on ice. 50% slurry amylose resin (New England Biolabs) was equilibrated with column buffer and a 7 ml volume was added to the supernatant and the 50 ml tube shook for 1 hour at 4° C. The cell lysate-amylose resin mixture was transferred to an ECONO-PAC® column (Bio-Rad Laboratories, Hercules, Calif.) and the supernatant was allowed to flow through. The remaining amylose beads bound with MBP-huHAO2 fusion protein were washed three times with 20 ml of column buffer and the MBP-huHAO2 protein was eluted with 5 additions of 2 ml elution buffer (column buffer containing 10 mM maltose, provided by Sigma-Aldrich). The protein was detected by the Bio-Rad protein assay and the fractions containing the fusion protein were combined (approximately a 4 ml volume). Glycerol (Sigma-Aldrich) was added to a final concentration of 10% and the solution was mixed well, aliquotted at 200 µl per tube, and stored at −80° C.

Mouse Hao2:

Purified, full-length cDNA encoding mouse Hao3 and the vector pET28a were digested with the restriction enzymes BamHI and NotI (Invitrogen) overnight at 37° C. The digested mouse Hao3 and pET28a vector were purified, ligated, and transformed into TOP-10 *E. coli* competent cells (Invitrogen) as described above for the MBP-huHAO2 with the exception of 30 µg/ml Kanamycin (Invitrogen) as the selection agent. Again, identical to the protocol described for MBP-huHAO2, positive colonies were picked, minipreps were grown and screened by BamHI and NotI restriction digestion, and run on a 1% agarose gel. As mentioned above, bacterial clones containing the proper plasmid and mouse Hao3 insert were grown in a 100 ml volume under selection for midi-prep production and sequencing to confirm accuracy. The plasmid that contained the full length mouse Hao3 sequence was called pET28a-muHAO3 and encoded a histidine tagged-Hao2 fusion protein.

Purified pET28a-muHAO3 plasmid was transformed into BL21-codonplus-RIPL competent cells and the cells were cultured and a cell pellet harvested exactly as described for MBP-huHAO2 with the exception of the selection agent being 30 μg/ml kanamycin.

The BL21 cell pellet containing His-muHAO3 (wet weight 6-8 g) was purified using the Ni-NTA purification system (Invitrogen). Briefly, cell pellets were resuspended in 35 ml of ice cold native binding buffer (native purification buffer (50 mM $NaH_2PO_4$ at pH 8.0, 500 mM NaCl) plus 10 mM imidazole at pH 8.0) supplemented with 0.4 ml of protease inhibitor cocktail set II. Cells were lysed by French Press at 4° C. and the lysate was centrifuged at 12,000×g for 30 minutes at 4° C. The supernatant was transferred to a fresh 50 ml Falcon tube and stored on ice. Ni-NTA agarose resin was equilibrated with native binding buffer and a 5 ml volume was added to the cell lysate and incubated at 4° C. with gentle shaking for 45 minutes. The cell lysate-Ni NTA resin mixture was transferred to an ECONO-PAC® column and the supernatant was allowed to flow through. The remaining resin bound with His-muHAO3 protein was washed three times with 20 ml of native washing buffer and the His-muHAO3 protein was eluted by five additions of 2 ml native elution buffer (native purification buffer plus 250 mM imidazole). Finally, the protein was detected, pooled, and aliquotted exactly as described for MBP-huHAO2.

Example 3

This example describes an assay that can be used to measure L-2-hydroxy acid oxidase activity in vitro.

Measurement of Hydroxyl Acid Oxidase:

The hydroxyl acid oxidase activity of the Hao enzymes was assayed for oxidation of the enzyme substrate 2-hydroxyoctanoate by monitoring the coupled reduction of 2,6-dichloroindophenol (DCIP) at 605 nm.

Figure 1A:
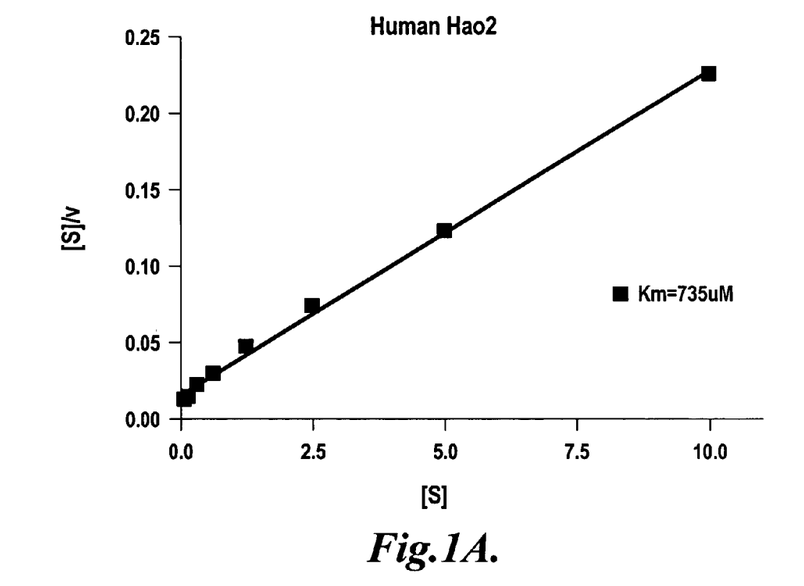
FIG. 1A graphically illustrates the Km determination for human Hao2 enzyme activity against the substrate 2-hydroxyoctanoate, as described in EXAMPLE 3.
Figure 1B:
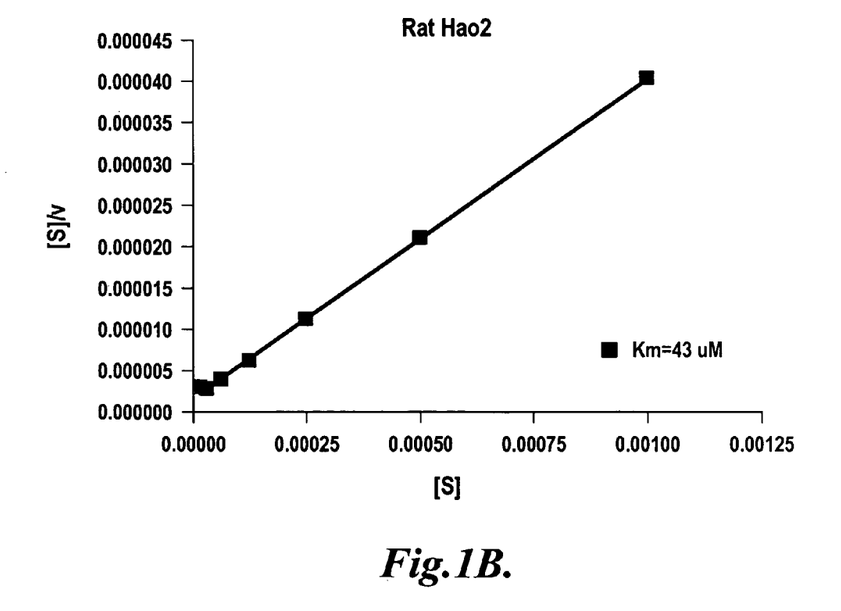
FIG. 1B graphically illustrates the Km determination for rat Hao2 enzyme activity against the substrate 2-hydroxyoctanoate, as described in EXAMPLE 3.
Figure 1C:
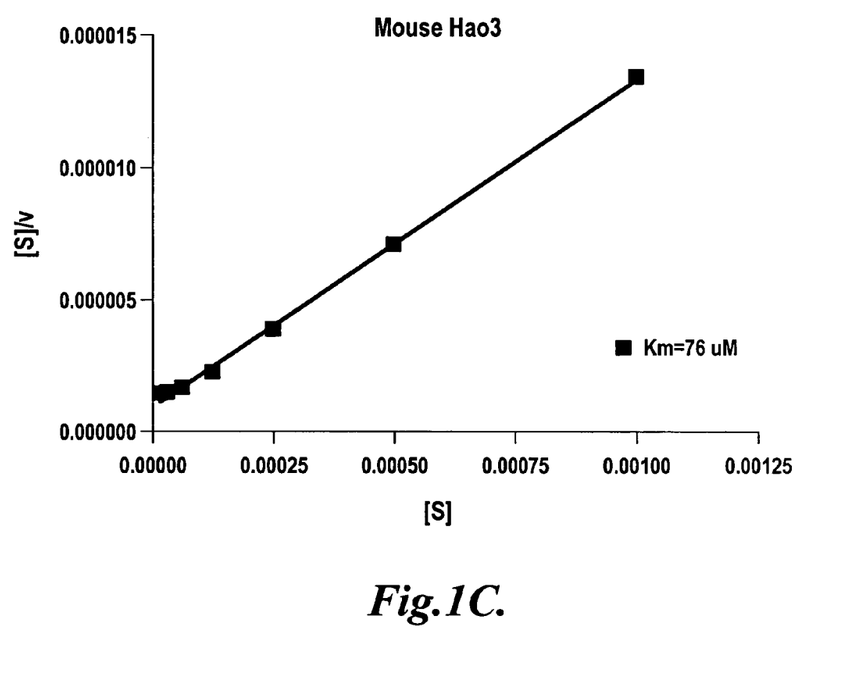
FIG. 1C graphically illustrates the Km determination for mouse Hao3 enzyme activity against the substrate 2-hydroxyoctanoate, as described in EXAMPLE 3.

In order to determine the Km of the enzyme for a given substrate, 20 μl/well of various concentrations of the substrate 2-hydroxyoctanoate were diluted in the assay buffer (100 mM Kpi, 1 mM EDTA and 0.1% BSA) and 175 μl/well of 50 μM 2-6-dichloroindophenol (DCIP) diluted in the same assay buffer was added to a 96-well plate. The reaction was started by the addition of 5 μl/well of the Hao enzyme, and the change in A605 at room temperature (18° C.) was measured over time. Km values were obtained by plotting the substrate concentration [S] versus reaction rates [S]/v, as shown in FIGS. 1A-C. An extinction coefficient of 110.26 $μM^{-1}$ $cm^{-1}$ for DCIP at 605 nm may be used for all calculations. One unit of activity may be defined as the reduction of 1 μmol of DCIP in 1 min (see Jones, J. M., et al., *J. Biol. Chem.* 275:12590-12597, 2000).

Results:

As shown in FIG. 1A, human Hao2 enzyme activity against the substrate 2-hydroxyoctanoate had a Km=735 μM. As shown in FIG. 1B, rat Hao2 enzyme activity against the substrate 2-hydroxyoctanoate had a Km=43 μM. As shown in FIG. 1C, mouse Hao3 enzyme activity against the substrate 2-hydroxyoctanoate had a Km=76 μM.

Example 4

This example describes an in vitro assay for screening inhibitors of the Hao enzyme.

Methods:

The following in vitro assay was carried out to screen for inhibitors of the Hao enzyme. 20 μl/well of substrate in the assay buffer (100 mM Kpi, 1 mM EDTA and 0.1% BSA), with a final reaction concentration corresponding to the level equivalent to its respective Km (as described in EXAMPLE 3) was added to a 96-well plate. 2 μl/well of a range of concentrations of a candidate inhibitory compound were dissolved in 100% DMSO, for a final concentration of 1%. 173 μl/well of 50 μM 2-6-dichloroindophenol (DCIP) diluted in the same assay buffer was added to the 96-well plate. The reaction was started by the addition of 5 μ/well of the Hao enzyme, and the change in A605 at room temperature (18° C.) was measured over time. The $IC_{50}$ of the compounds that were identified as inhibitors of Hao enzyme were obtained by plotting the compound concentration versus reaction rates.

Results:

Hao inhibitory compounds were identified using the assay described above. IC50 values of exemplary Hao inhibitory compounds are listed below in TABLE 2.

TABLE 2

| Exemplary Hao Inhibitory compounds against mouse Hao3 | |
|---|---|
| Compound | IC50 |
| Compound A | 447 nM |
| Compound B | 1.4 μM |
| Compound C | 1.72 μM |
| Compound D | 3.28 μM |

The Hao inhibitory compounds identified using the described methods may be used to modulate the activity of L-2-hydroxy acid oxidases in mammals in order to ameliorate one or more symptoms associated with Metabolic Syndrome.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for testing if a chemical agent identified as a chemical agent that decreases the enzymatic activity of an L-2 hydroxy acid oxidase in an in vitro assay decreases the enzymatic activity of an L-2 hydroxy acid oxidase in vivo, comprising administering one or more chemical agents that decrease L-2 hydroxy acid oxidase activity in vitro to a test animal and measuring one or more physiological parameters selected from the group consisting of body weight, body fat, retroperitoneal fat accumulation, serum level of LDL-cholesterol, serum level of HDL-cholesterol, and leptin expression, wherein a decrease in at least one of body weight, body fat, retroperitoneal fat accumulation, serum LDL cholesterol, or leptin expression, in comparison to a control animal not administered the chemical agent, indicates that the chemical agent identified in the in vitro assay decreases the enzymatic activity of an L-2 hydroxy acid oxidase in vivo.

2. The method of claim 1, wherein the measured physiological parameter is body weight.

3. The method of claim 1, wherein the in vitro assay comprises the steps of:
   (a) contacting an L-2-hydroxy acid oxidase, in a solution in vitro, with one or more chemical agents in the presence of a substrate that is capable of being oxidized by the L-2-hydroxy acid oxidase;
   (b) measuring the enzymatic activity of the L-2 hydroxy acid oxidase in the presence of the chemical agent; and
   (c) comparing the enzymatic activity of the L-2-hydroxy acid oxidase in the presence of the chemical agent to the activity of L-2-hydroxy acid oxidase in the absence of the chemical agent, wherein enzymatic activity in the presence of the chemical agent that is less than the enzymatic activity in the absence of the chemical agent identifies a chemical agent that decreases the enzymatic activity of the L-2-hydroxy acid oxidase.

4. The method of claim 3, wherein the solution further includes 2,6-dichloroindophenol (DCIP), and wherein the enzymatic activity of L-2-hydroxy acid oxidase is determined by measuring reduction of DCIP upon oxidation of the substrate.

5. The method of claim 4, wherein the reduction of DCIP is monitored by measuring light absorption of the solution.

6. The method of claim 1, wherein the chemical agent is a chemical compound.

7. The method of claim 1, wherein the chemical agent is a protein.

8. The method of claim 3, wherein the solution comprises KPi and EDTA.

9. The method of claim 3, wherein the substrate is L-2 hydroxy-octanoate.

10. The method of claim 3, wherein the substrate is mandelate.

11. The method of claim 1, wherein the L-2-hydroxy acid oxidase is capable of oxidizing a 2-hydroxy acid substrate and comprises an amino acid sequence at least 90% identical to an L-2-hydroxy acid oxidase consisting of the amino acid sequence set forth in SEQ ID NO:2.

12. The method of claim 1, wherein the L-2-hydroxy acid oxidase is capable of oxidizing a 2-hydroxy acid substrate and comprises an amino acid sequence at least 90% identical to an L-2-hydroxy acid oxidase consisting of the amino acid sequence set forth in SEQ ID NO:6.

13. The method of claim 3, wherein steps (a)-(c) are automated.

\* \* \* \* \*

SEQUENCE LISTING

```
<160> NUMBER OF SEQ ID NOS: 10

<210> SEQ ID NO 1
<211> LENGTH: 2029
<212> TYPE: DNA
<213> ORGANISM: Mus musculus
<220> FEATURE:
<221> NAME/KEY: CDS
<222> LOCATION: (223)..(1284)
```

-continued

```
<400> SEQUENCE: 1
ccacgcgtcc ggacccacgc gtccgcccac gcgtccgccc acgcgtccgg gctttgcatg      60
gctacctcta catactgcta ttgctggcta ttggaagacc ttagtgtcag aatcttcttg     120
tgtacaagcc ctgaatggtg tgaccaaccc aagttcctac agcatctttg cagctgttga    180
tctcactctt tcgttcctat tggagaaact accggcccag ca atg tct ttg ctg       234
                                                Met Ser Leu Leu
                                                 1 tgt ttg gca gac ttt aag gca caa gca caa aag cag ctg tct aag acc      282
Cys Leu Ala Asp Phe Lys Ala Gln Ala Gln Lys Gln Leu Ser Lys Thr
 5              10                  15                  20 tcc tgg gat ttt att gaa gga gaa gct gat gat ggc ata acc tac aat      330
Ser Trp Asp Phe Ile Glu Gly Glu Ala Asp Asp Gly Ile Thr Tyr Asn
                25                  30                  35 gac aac ttg gca gca ttt aga aga atc cgc ctc cgc ccc aga tac ctg      378
Asp Asn Leu Ala Ala Phe Arg Arg Ile Arg Leu Arg Pro Arg Tyr Leu
         40                  45                  50 aga gat gtg tca aag ata gac acc agg acc aca atc caa ggg cag gag      426
Arg Asp Val Ser Lys Ile Asp Thr Arg Thr Thr Ile Gln Gly Gln Glu
     55                  60                  65 atc aat gcc ccc att tgc atc tca ccc aca gcc ttt cat tca att gcc      474
Ile Asn Ala Pro Ile Cys Ile Ser Pro Thr Ala Phe His Ser Ile Ala
 70                  75                  80 tgg gca gat gga gaa aag agc aca gct aaa gct gct cag aag gcc aac      522
Trp Ala Asp Gly Glu Lys Ser Thr Ala Lys Ala Ala Gln Lys Ala Asn
85                  90                  95                  100 atc tgc tat gtc atc agc agt tat gcc agc tat act gtg gaa gac att      570
Ile Cys Tyr Val Ile Ser Ser Tyr Ala Ser Tyr Thr Val Glu Asp Ile
                105                 110                 115 gtt gct gct gcc cct gga ggc ctc cat tgg ttc caa ctt tat gtg cag      618
Val Ala Ala Ala Pro Gly Gly Leu His Trp Phe Gln Leu Tyr Val Gln
        120                 125                 130 cca gac tgg gac atc aac aag cag atg gtt cag agg ata gaa gcc ttg      666
Pro Asp Trp Asp Ile Asn Lys Gln Met Val Gln Arg Ile Glu Ala Leu
    135                 140                 145 ggt ttc aaa gct ttg gtg gtc act gta gat gcg cct gta ctt ggc aat      714
Gly Phe Lys Ala Leu Val Val Thr Val Asp Ala Pro Val Leu Gly Asn
150                 155                 160 agg cga ggg aac aag aga agc ctg ctg gat ttg gag gca aac ata aag      762
Arg Arg Gly Asn Lys Arg Ser Leu Leu Asp Leu Glu Ala Asn Ile Lys
165                 170                 175                 180 ctg aag gat ctc cga tcc cct gga gag agc aag tct gga ctt cct act      810
Leu Lys Asp Leu Arg Ser Pro Gly Glu Ser Lys Ser Gly Leu Pro Thr
                185                 190                 195 ccc ctg tct atg cca agt aca tct tcc tgc tgg aat gat ctc ccc ttg      858
Pro Leu Ser Met Pro Ser Thr Ser Ser Cys Trp Asn Asp Leu Pro Leu
        200                 205                 210 ctt cag agt atg act cgg ttg ccc att atc ctc aaa ggg att ttg aca      906
Leu Gln Ser Met Thr Arg Leu Pro Ile Ile Leu Lys Gly Ile Leu Thr
    215                 220                 225 aaa gag gat gca gaa tta gca gtg aag cac aac atc cga ggc atc att      954
Lys Glu Asp Ala Glu Leu Ala Val Lys His Asn Ile Arg Gly Ile Ile
230                 235                 240 gtt tcc aac cat ggc ggg agg cag ctt gat gag gtt cct gca tct att     1002
Val Ser Asn His Gly Gly Arg Gln Leu Asp Glu Val Pro Ala Ser Ile
245                 250                 255                 260 gat gct ctg aga gaa gtg gtg gct gcc gtc aat ggg aaa att gaa gtg     1050
Asp Ala Leu Arg Glu Val Val Ala Ala Val Asn Gly Lys Ile Glu Val
```

```
                    265                 270                 275
tac atg gat ggt ggg gtt cga acc ggc aat gat gtg ttg aag gca cta    1098
Tyr Met Asp Gly Gly Val Arg Thr Gly Asn Asp Val Leu Lys Ala Leu
            280                 285                 290 gcc ctt gga gct agg tgc att ttt ctt ggg aga cca atc att tgg ggc    1146
Ala Leu Gly Ala Arg Cys Ile Phe Leu Gly Arg Pro Ile Ile Trp Gly
        295                 300                 305 ctt gcc tgc aag ggt gaa gat ggt gtt aag gaa gtt tta gat att cta    1194
Leu Ala Cys Lys Gly Glu Asp Gly Val Lys Glu Val Leu Asp Ile Leu
    310                 315                 320 aaa gaa gaa ctc cac act tgt atg gcc ctt tca ggc tgc cgg tca gtt    1242
Lys Glu Glu Leu His Thr Cys Met Ala Leu Ser Gly Cys Arg Ser Val
325                 330                 335                 340 gct gag atc agt cca gac ctg att cag ttc tcc aga tta taa            1284
Ala Glu Ile Ser Pro Asp Leu Ile Gln Phe Ser Arg Leu
                345                 350 ggacctactg agattgccta caagagaaag acaagctttc aacatagtgt gtgatgctgt    1344
tcttcttggg tccattcat aatagaagtt taagccctct accctcaaaa attgagacag    1404
atggagaaaa gataggctac agctaccaga gggtgcattt ggatgaagaa ataacatcta    1464
atgttctaca ggaaactaga gttaacaatt aattgactat atcaaaaagc catgttctag    1524
caagaaagga aatagttaga tctgatgtga cataccagtt accttcattt gatcagtagt    1584
gcattataca taattgaaat gtcatactgt gccataatta tgtgtaatta ctatgtatca    1644
attaaaatat caatatatgt tcaaaaagaa atggggacag ggttatcctg attttattca    1704
ttccctcctg caagaaatat ttttaaaaca tcaatatatg tagtcaaatt ctgaagcata    1764
gtacagcatg tgaattattc aagtttctgt cacagcatgt tacagaaata ttatgatcta    1824
ttgcctaatg tccattgtta acagaagctg acctcaataa aaaacaaga ggaagatttt     1884 gaaactcata tttaaaactt tatgactaaa ttaaaattaa atattccagt catttactga    1944
tacatgaaaa agaagatatc tttattctgg tcataatcat tttgtcaaat aaatctaagc    2004
cttttcaatg aaaaaaaaaa aaaaa                                          2029

<210> SEQ ID NO 2
<211> LENGTH: 353
<212> TYPE: PRT
<213> ORGANISM: Mus musculus

<400> SEQUENCE: 2

Met Ser Leu Leu Cys Leu Ala Asp Phe Lys Ala Gln Ala Gln Lys Gln
1               5                   10                  15

Leu Ser Lys Thr Ser Trp Asp Phe Ile Glu Gly Glu Ala Asp Asp Gly
            20                  25                  30

Ile Thr Tyr Asn Asp Asn Leu Ala Ala Phe Arg Arg Ile Arg Leu Arg
        35                  40                  45

Pro Arg Tyr Leu Arg Asp Val Ser Lys Ile Asp Thr Arg Thr Thr Ile
    50                  55                  60

Gln Gly Gln Glu Ile Asn Ala Pro Ile Cys Ile Ser Pro Thr Ala Phe
65                  70                  75                  80

His Ser Ile Ala Trp Ala Asp Gly Glu Lys Ser Thr Ala Lys Ala Ala
                85                  90                  95

Gln Lys Ala Asn Ile Cys Tyr Val Ile Ser Ser Tyr Ala Ser Tyr Thr
            100                 105                 110

Val Glu Asp Ile Val Ala Ala Ala Pro Gly Gly Leu His Trp Phe Gln
        115                 120                 125
```

```
Leu Tyr Val Gln Pro Asp Trp Asp Ile Asn Lys Gln Met Val Gln Arg
        130                 135                 140

Ile Glu Ala Leu Gly Phe Lys Ala Leu Val Thr Val Asp Ala Pro
145                 150                 155                 160

Val Leu Gly Asn Arg Gly Asn Lys Arg Ser Leu Leu Asp Leu Glu
            165                 170                 175

Ala Asn Ile Lys Leu Lys Asp Leu Arg Ser Pro Gly Glu Ser Lys Ser
            180                 185                 190

Gly Leu Pro Thr Pro Leu Ser Met Pro Ser Thr Ser Ser Cys Trp Asn
            195                 200                 205

Asp Leu Pro Leu Leu Gln Ser Met Thr Arg Leu Pro Ile Ile Leu Lys
        210                 215                 220

Gly Ile Leu Thr Lys Glu Asp Ala Glu Leu Ala Val Lys His Asn Ile
225                 230                 235                 240

Arg Gly Ile Ile Val Ser Asn His Gly Gly Arg Gln Leu Asp Glu Val
                245                 250                 255

Pro Ala Ser Ile Asp Ala Leu Arg Glu Val Val Ala Ala Val Asn Gly
            260                 265                 270

Lys Ile Glu Val Tyr Met Asp Gly Gly Val Arg Thr Gly Asn Asp Val
275                 280                 285

Leu Lys Ala Leu Ala Leu Gly Ala Arg Cys Ile Phe Leu Gly Arg Pro
        290                 295                 300

Ile Ile Trp Gly Leu Ala Cys Lys Gly Glu Asp Gly Val Lys Glu Val
305                 310                 315                 320

Leu Asp Ile Leu Lys Glu Glu Leu His Thr Cys Met Ala Leu Ser Gly
                325                 330                 335

Cys Arg Ser Val Ala Glu Ile Ser Pro Asp Leu Ile Gln Phe Ser Arg
                340                 345                 350

Leu

<210> SEQ ID NO 3
<211> LENGTH: 1648
<212> TYPE: DNA
<213> ORGANISM: Rattus norvegicus
<220> FEATURE:
<221> NAME/KEY: CDS
<222> LOCATION: (203)..(1264)

<400> SEQUENCE: 3
gagagctggg caatgaacca ctgtagcggg ctttgcattg ctgcctctac ctacagctat      60
tactggtcat tggaagacct tagagtcaga atcttcttgt gtaagagccc tgaatgctgt    120
gaccaacccc agtgtctaca gcatctttgc agctgttaat ctcactgttc tcgttcctat    180
tgaagaaatt actggcccag aa atg cct ttg gtg tgt ttg gca gac ttt aag    232
                        Met Pro Leu Val Cys Leu Ala Asp Phe Lys
                          1               5                  10 gca cat gcg caa aag cag ctg tct aag acc tcc tgg gac ttt att gaa    280
Ala His Ala Gln Lys Gln Leu Ser Lys Thr Ser Trp Asp Phe Ile Glu
             15                  20                  25 gga gaa gct gac gac ggc atc acc tac agt gag aac ata gca gca ttt    328
Gly Glu Ala Asp Asp Gly Ile Thr Tyr Ser Glu Asn Ile Ala Ala Phe
         30                  35                  40 aaa aga atc cgc ctc cgc ccc cga tac ctg aga gat atg tca aag gtg    376
Lys Arg Ile Arg Leu Arg Pro Arg Tyr Leu Arg Asp Met Ser Lys Val
     45                  50                  55 gac acc agg acc aca atc caa ggg cag gag atc agt gct ccc atc tgc    424
```

```
                                                        -continued

Asp Thr Arg Thr Thr Ile Gln Gly Gln Glu Ile Ser Ala Pro Ile Cys
 60              65                  70 atc tca ccc aca gcc ttt cac tcc att gcc tgg ccg gat gga gaa aag    472
Ile Ser Pro Thr Ala Phe His Ser Ile Ala Trp Pro Asp Gly Glu Lys
 75              80                  85                  90 agc aca gct aga gct gct cag gag gcc aac atc tgc tat gtc atc agc    520
Ser Thr Ala Arg Ala Ala Gln Glu Ala Asn Ile Cys Tyr Val Ile Ser
                 95                 100                 105 agt tat gcc agc tat tcc ctg gaa gat att gtt gct gct gcc ccc gaa    568
Ser Tyr Ala Ser Tyr Ser Leu Glu Asp Ile Val Ala Ala Pro Glu
                110                 115                 120 ggc ttt cgt tgg ttc caa ctc tac atg aag tca gac tgg gac ttc aac    616
Gly Phe Arg Trp Phe Gln Leu Tyr Met Lys Ser Asp Trp Asp Phe Asn
            125                 130                 135 aag cag atg gtt cag agg gca gaa gcc ttg ggt ttc aaa gct ttg gtg    664
Lys Gln Met Val Gln Arg Ala Glu Ala Leu Gly Phe Lys Ala Leu Val
        140                 145                 150 atc act ata gat acg cct gta ctt ggc aat agg cga cgg gac aag aga    712
Ile Thr Ile Asp Thr Pro Val Leu Gly Asn Arg Arg Arg Asp Lys Arg
155                 160                 165                 170 aac cag ctg aat ttg gag gca aac ata ttg ttg aag gat ctc cga gcc    760
Asn Gln Leu Asn Leu Glu Ala Asn Ile Leu Leu Lys Asp Leu Arg Ala
                175                 180                 185 ctc aaa gag gaa aag ccc aca cag tct gtg ccc gtg tct ttt ccg aaa    808
Leu Lys Glu Glu Lys Pro Thr Gln Ser Val Pro Val Ser Phe Pro Lys
            190                 195                 200 gca tct ttc tgc tgg aat gat ctt tcc ttg ctt cag agt ata act cgg    856
Ala Ser Phe Cys Trp Asn Asp Leu Ser Leu Leu Gln Ser Ile Thr Arg
        205                 210                 215 ttg ccc att atc ctc aaa ggg att ttg acg aaa gag gat gca gag tta    904
Leu Pro Ile Ile Leu Lys Gly Ile Leu Thr Lys Glu Asp Ala Glu Leu
220                 225                 230 gca atg aag cac aac gtc caa ggc atc gtt gtt tcc aac cat ggt ggg    952
Ala Met Lys His Asn Val Gln Gly Ile Val Val Ser Asn His Gly Gly
235                 240                 245                 250 agg cag ctt gat gag gtt tct gct tca att gat gct ctg aga gaa gtg   1000
Arg Gln Leu Asp Glu Val Ser Ala Ser Ile Asp Ala Leu Arg Glu Val
                255                 260                 265 gtg gct gct gtc aaa ggg aaa att gaa gtg tac atg gat ggt ggg gtt   1048
Val Ala Ala Val Lys Gly Lys Ile Glu Val Tyr Met Asp Gly Gly Val
            270                 275                 280 cga act ggc act gat gtg ttg aag gca ctg gcc ctt gga gct agg tgc   1096
Arg Thr Gly Thr Asp Val Leu Lys Ala Leu Ala Leu Gly Ala Arg Cys
        285                 290                 295 att ttt ctt ggg aga cca atc ctt tgg ggc ctt gcc tgc aag ggt gaa   1144
Ile Phe Leu Gly Arg Pro Ile Leu Trp Gly Leu Ala Cys Lys Gly Glu
300                 305                 310 gat ggt gtt aag gaa gtt tta gat att cta aca gca gaa ctc cat aga   1192
Asp Gly Val Lys Glu Val Leu Asp Ile Leu Thr Ala Glu Leu His Arg
315                 320                 325                 330 tgt atg acc ctt tca ggc tgc cag tca gtt gct gag att agt cca gac   1240
Cys Met Thr Leu Ser Gly Cys Gln Ser Val Ala Glu Ile Ser Pro Asp
                335                 340                 345 ctg att cag ttc tcc aga tta taa ggacctactg agatccctac aagaggaaga   1294
Leu Ile Gln Phe Ser Arg Leu
                350 caagacttca acatagtgtg tgagcctatt cttcttcggt ccgatcatac ctagtagttt   1354 gagccctcta ccttgagaaa tccagatcga tgaagaaaag atagctaaca gctaccagag   1414
```

-continued

```
gggtgcattt ggatgaagga ataacatcta atgttctaca ggataactat aactgacaat    1474
taattgacta tgtccaatag ccatgttcca gaaagaaagg aaatagttac atctggtgtg    1534
acatgccaat tactttcatt tgattattat gtacactata cattattaaa acgtcatact    1594
gtgccataat tatgtgcaat tactatgtat caattaaaac aacatatat  attt          1648
```

<210> SEQ ID NO 4
<211> LENGTH: 353
<212> TYPE: PRT
<213> ORGANISM: Rattus norvegicus

<400> SEQUENCE: 4

```
Met Pro Leu Val Cys Leu Ala Asp Phe Lys Ala His Ala Gln Lys Gln
 1               5                  10                  15

Leu Ser Lys Thr Ser Trp Asp Phe Ile Glu Gly Glu Ala Asp Asp Gly
            20                  25                  30

Ile Thr Tyr Ser Glu Asn Ile Ala Ala Phe Lys Arg Ile Arg Leu Arg
        35                  40                  45

Pro Arg Tyr Leu Arg Asp Met Ser Lys Val Asp Arg Thr Thr Ile
 50                  55                  60

Gln Gly Gln Glu Ile Ser Ala Pro Ile Cys Ile Ser Pro Thr Ala Phe
 65                  70                  75                  80

His Ser Ile Ala Trp Pro Asp Gly Glu Lys Ser Thr Ala Arg Ala Ala
                85                  90                  95

Gln Glu Ala Asn Ile Cys Tyr Val Ile Ser Ser Tyr Ala Ser Tyr Ser
            100                 105                 110

Leu Glu Asp Ile Val Ala Ala Pro Glu Gly Phe Arg Trp Phe Gln
        115                 120                 125

Leu Tyr Met Lys Ser Asp Trp Asp Phe Asn Lys Gln Met Val Gln Arg
130                 135                 140

Ala Glu Ala Leu Gly Phe Lys Ala Leu Val Ile Thr Ile Asp Thr Pro
145                 150                 155                 160

Val Leu Gly Asn Arg Arg Arg Asp Lys Arg Asn Gln Leu Asn Leu Glu
                165                 170                 175

Ala Asn Ile Leu Leu Lys Asp Leu Arg Ala Leu Lys Glu Glu Lys Pro
            180                 185                 190

Thr Gln Ser Val Pro Val Ser Phe Pro Lys Ala Ser Phe Cys Trp Asn
        195                 200                 205

Asp Leu Ser Leu Leu Gln Ser Ile Thr Arg Leu Pro Ile Ile Leu Lys
210                 215                 220

Gly Ile Leu Thr Lys Glu Asp Ala Glu Leu Ala Met Lys His Asn Val
225                 230                 235                 240

Gln Gly Ile Val Val Ser Asn His Gly Gly Arg Gln Leu Asp Glu Val
                245                 250                 255

Ser Ala Ser Ile Asp Ala Leu Arg Glu Val Val Ala Ala Val Lys Gly
            260                 265                 270

Lys Ile Glu Val Tyr Met Asp Gly Gly Val Arg Thr Gly Thr Asp Val
        275                 280                 285

Leu Lys Ala Leu Ala Leu Gly Ala Arg Cys Ile Phe Leu Gly Arg Pro
290                 295                 300

Ile Leu Trp Gly Leu Ala Cys Lys Gly Glu Asp Gly Val Lys Glu Val
305                 310                 315                 320

Leu Asp Ile Leu Thr Ala Glu Leu His Arg Cys Met Thr Leu Ser Gly
                325                 330                 335
```

```
                Cys Gln Ser Val Ala Glu Ile Ser Pro Asp Leu Ile Gln Phe Ser Arg
                                340                 345                 350

Leu

<210> SEQ ID NO 5
<211> LENGTH: 1476
<212> TYPE: DNA
<213> ORGANISM: Homo sapiens
<220> FEATURE:
<221> NAME/KEY: CDS
<222> LOCATION: (133)..(1188)

<400> SEQUENCE: 5
ttctttagcc tgaactgtgg gtagtgatgt ggtgtgtttc ctaacacctc cggcagtgag      60
ccaggctttg agtggctgcg tctaaacact tctttccctg aggactggaa gacattagaa     120
taaggtccag aa atg tcc ttg gtg tgt ttg aca gac ttt cag gcc cat gcg     171
              Met Ser Leu Val Cys Leu Thr Asp Phe Gln Ala His Ala
                1               5                  10 cga gag cag ctg tct aag tca act cgg gat ttt att gaa ggt gga gca       219
Arg Glu Gln Leu Ser Lys Ser Thr Arg Asp Phe Ile Glu Gly Gly Ala
         15                  20                  25 gat gac agc atc acg cgg gat gac aac att gca gca ttt aaa aga att      267
Asp Asp Ser Ile Thr Arg Asp Asp Asn Ile Ala Ala Phe Lys Arg Ile
 30                  35                  40                  45 cgc ctc cgt ccg cgg tac ctg aga gat gtg tct gag gtg gac acc aga      315
Arg Leu Arg Pro Arg Tyr Leu Arg Asp Val Ser Glu Val Asp Thr Arg
                 50                  55                  60 acc aca atc caa ggg gag gag atc agt gcc cct att tgt atc gca ccc      363
Thr Thr Ile Gln Gly Glu Glu Ile Ser Ala Pro Ile Cys Ile Ala Pro
             65                  70                  75 aca ggg ttc cac tgc ctt gtc tgg cct gat ggg gaa atg agc aca gca      411
Thr Gly Phe His Cys Leu Val Trp Pro Asp Gly Glu Met Ser Thr Ala
         80                  85                  90 aga gct gcc caa gcg gct ggt atc tgc tac atc acc agc aca ttt gcc      459
Arg Ala Ala Gln Ala Ala Gly Ile Cys Tyr Ile Thr Ser Thr Phe Ala
 95                 100                 105 agc tgt agc ctt gaa gac att gtc att gca gct ccc gaa ggc ctc cga      507
Ser Cys Ser Leu Glu Asp Ile Val Ile Ala Ala Pro Glu Gly Leu Arg
110                 115                 120                 125 tgg ttc caa ctc tat gtg cat cca gac ctg cag ctg aac aaa cag ttg      555
Trp Phe Gln Leu Tyr Val His Pro Asp Leu Gln Leu Asn Lys Gln Leu
                130                 135                 140 atc cag agg gta gaa tcc cta ggt ttc aaa gct ttg gta ata act ttg      603
Ile Gln Arg Val Glu Ser Leu Gly Phe Lys Ala Leu Val Ile Thr Leu
            145                 150                 155 gat aca cct gta tgt ggc aac agg cga cat gac att cga aac cag ttg      651
Asp Thr Pro Val Cys Gly Asn Arg Arg His Asp Ile Arg Asn Gln Leu
        160                 165                 170 agg agg aac tta aca cta aca gat ctt caa tca cct aaa aag gga aat      699
Arg Arg Asn Leu Thr Leu Thr Asp Leu Gln Ser Pro Lys Lys Gly Asn
    175                 180                 185 gca ata cct tat ttc cag atg act cct atc agc act tct ctc tgc tgg      747
Ala Ile Pro Tyr Phe Gln Met Thr Pro Ile Ser Thr Ser Leu Cys Trp
190                 195                 200                 205 aat gat ctc tcc tgg ttt cag agc ata act cga ttg ccc atc atc ctg      795
Asn Asp Leu Ser Trp Phe Gln Ser Ile Thr Arg Leu Pro Ile Ile Leu
                210                 215                 220 aaa ggg att ttg aca aaa gag gat gca gag tta gct gtg aag cac aat      843
Lys Gly Ile Leu Thr Lys Glu Asp Ala Glu Leu Ala Val Lys His Asn
            225                 230                 235
```

-continued

```
gtc cag ggt atc att gtt tcc aac cat ggt ggg agg cag ctt gat gag      891
Val Gln Gly Ile Ile Val Ser Asn His Gly Gly Arg Gln Leu Asp Glu
        240                 245                 250 gtt ctt gct tca att gat gct ttg aca gaa gtg gtg gct gct gta aag      939
Val Leu Ala Ser Ile Asp Ala Leu Thr Glu Val Val Ala Ala Val Lys
    255                 260                 265 ggg aaa att gaa gtc tac ctg gat ggc ggg gtc cga act ggc aat gat      987
Gly Lys Ile Glu Val Tyr Leu Asp Gly Gly Val Arg Thr Gly Asn Asp
270                 275                 280                 285 gtg ctg aag gct ctg gcc ctt gga gct aag tgc att ttt ctt ggg aga     1035
Val Leu Lys Ala Leu Ala Leu Gly Ala Lys Cys Ile Phe Leu Gly Arg
                290                 295                 300 cca atc cta tgg ggc ctt gcc tgc aag ggt gaa cat ggt gtt aag gaa     1083
Pro Ile Leu Trp Gly Leu Ala Cys Lys Gly Glu His Gly Val Lys Glu
            305                 310                 315 gtt ttg aac att tta aca aat gag ttc cac act tcc atg gcc ctt aca     1131
Val Leu Asn Ile Leu Thr Asn Glu Phe His Thr Ser Met Ala Leu Thr
        320                 325                 330 ggc tgc cgg tcg gtc gct gag atc aat cga aac ttg gtc cag ttt tcc     1179
Gly Cys Arg Ser Val Ala Glu Ile Asn Arg Asn Leu Val Gln Phe Ser
    335                 340                 345 agg ctg taa gaaaaaggg ccaataacca gactgctgag gttgcccaca              1228
Arg Leu
350 ggaggatcac aaactcacag cacagtgtgt gatgctgtcc ttcctggacc ccattctgtc   1288 cggaggctca tggcccatat ttcccacatt tctaatacca ccaccctgt gcttcaggcc    1348 ctccaaaccc ctgtgttccc caaatgttcc atgcccttct ttgtatcact gactattata   1408 tgttgctctc ttgcctaaat cttcctctga agtaaaagat ctcaaaagga cagatcatta  1468 atgactgg                                                            1476
```

<210> SEQ ID NO 6
<211> LENGTH: 351
<212> TYPE: PRT
<213> ORGANISM: Homo sapiens

<400> SEQUENCE: 6

```
Met Ser Leu Val Cys Leu Thr Asp Phe Gln Ala His Ala Arg Glu Gln
1               5                   10                  15

Leu Ser Lys Ser Thr Arg Asp Phe Ile Glu Gly Gly Ala Asp Asp Ser
            20                  25                  30

Ile Thr Arg Asp Asp Asn Ile Ala Ala Phe Lys Arg Ile Arg Leu Arg
        35                  40                  45

Pro Arg Tyr Leu Arg Asp Val Ser Glu Val Asp Thr Arg Thr Thr Ile
    50                  55                  60

Gln Gly Glu Glu Ile Ser Ala Pro Ile Cys Ile Ala Pro Thr Gly Phe
65                  70                  75                  80

His Cys Leu Val Trp Pro Asp Gly Glu Met Ser Thr Ala Arg Ala Ala
                85                  90                  95

Gln Ala Ala Gly Ile Cys Tyr Ile Thr Ser Thr Phe Ala Ser Cys Ser
            100                 105                 110

Leu Glu Asp Ile Val Ile Ala Ala Pro Glu Gly Leu Arg Trp Phe Gln
        115                 120                 125

Leu Tyr Val His Pro Asp Leu Gln Leu Asn Lys Gln Leu Ile Gln Arg
    130                 135                 140

Val Glu Ser Leu Gly Phe Lys Ala Leu Val Ile Thr Leu Asp Thr Pro
```

```
                145                 150                 155                 160
    Val Cys Gly Asn Arg Arg His Asp Ile Arg Asn Gln Leu Arg Arg Asn
                    165                 170                 175

Leu Thr Leu Thr Asp Leu Gln Ser Pro Lys Lys Gly Asn Ala Ile Pro
                    180                 185                 190

Tyr Phe Gln Met Thr Pro Ile Ser Thr Ser Leu Cys Trp Asn Asp Leu
                    195                 200                 205

Ser Trp Phe Gln Ser Ile Thr Arg Leu Pro Ile Ile Leu Lys Gly Ile
        210                 215                 220

Leu Thr Lys Glu Asp Ala Glu Leu Ala Val Lys His Asn Val Gln Gly
    225                 230                 235                 240

Ile Ile Val Ser Asn His Gly Gly Arg Gln Leu Asp Glu Val Leu Ala
                    245                 250                 255

Ser Ile Asp Ala Leu Thr Glu Val Val Ala Ala Val Lys Gly Lys Ile
                    260                 265                 270

Glu Val Tyr Leu Asp Gly Gly Val Arg Thr Gly Asn Asp Val Leu Lys
                    275                 280                 285

Ala Leu Ala Leu Gly Ala Lys Cys Ile Phe Leu Gly Arg Pro Ile Leu
        290                 295                 300

Trp Gly Leu Ala Cys Lys Gly Glu His Gly Val Lys Glu Val Leu Asn
    305                 310                 315                 320

Ile Leu Thr Asn Glu Phe His Thr Ser Met Ala Leu Thr Gly Cys Arg
                    325                 330                 335

Ser Val Ala Glu Ile Asn Arg Asn Leu Val Gln Phe Ser Arg Leu
                    340                 345                 350

<210> SEQ ID NO 7
<211> LENGTH: 34
<212> TYPE: DNA
<213> ORGANISM: Artificial Sequence
<220> FEATURE:
<223> OTHER INFORMATION: Synthetic

<400> SEQUENCE: 7
gcgggatcca tgtctttgct gtgtttggca gact                              34

<210> SEQ ID NO 8
<211> LENGTH: 42
<212> TYPE: DNA
<213> ORGANISM: Artificial Sequence
<220> FEATURE:
<223> OTHER INFORMATION: Synthetic

<400> SEQUENCE: 8
ataagaatgc ggccgcttat aatctggaga actgaatcag gt                     42

<210> SEQ ID NO 9
<211> LENGTH: 33
<212> TYPE: DNA
<213> ORGANISM: Artificial Sequence
<220> FEATURE:
<223> OTHER INFORMATION: Synthetic

<400> SEQUENCE: 9
gcgggatcca tgtccttggt gtgtctgaca gac                               33

<210> SEQ ID NO 10
<211> LENGTH: 42
<212> TYPE: DNA
<213> ORGANISM: Artificial Sequence
```

```
-continued

<220> FEATURE:
<223> OTHER INFORMATION: Synthetic

<400> SEQUENCE: 10
ataagaatgc ggccgcttat aatctggaga actgaatcag gt                              42
```